United States Patent [19]

Roshdy

[11] Patent Number: 4,549,649

[45] Date of Patent: Oct. 29, 1985

[54] UNITARY ARMED SUTURE MOUNTING BOARD

[75] Inventor: Constance E. Roshdy, North Brunswick, N.J.

[73] Assignee: Ethicon, Inc., Somerville, N.J.

[21] Appl. No.: 646,727

[22] Filed: Sep. 4, 1984

Related U.S. Application Data

[63] Continuation-in-part of Ser. No. 555,724, Nov. 28, 1983.

[51] Int. Cl.[4] .............................................. A61B 17/06
[52] U.S. Cl. .................................... 206/63.3; 206/380
[58] Field of Search .................... 206/63.3, 480, 380, 206/382, 383

[56] References Cited

U.S. PATENT DOCUMENTS

| | | | |
|---|---|---|---|
| 3,728,839 | 4/1973 | Glick | 206/63.3 |
| 4,120,395 | 10/1978 | Mandel et al. | 206/63.3 |
| 4,135,623 | 1/1979 | Thyen | 206/63.3 |
| 4,183,431 | 1/1980 | Schmidt et al. | 206/63.3 |
| 4,258,843 | 3/1981 | Wymer | 206/63.3 |
| 4,287,987 | 9/1981 | Hoffman et al. | 206/63.3 |
| 4,391,365 | 7/1983 | Batchelor | 206/63.3 |

*Primary Examiner*—Joseph Man-Fu Moy
*Attorney, Agent, or Firm*—Charles J. Metz

[57] ABSTRACT

The invention provides an element for holding a needled suture comprising a suture strand having at least one end attached to a needle and having a first portion of said strand remote from the end attached to said needle and a second portion of said strand intermediate said first portion and the end attached to said needle, said element comprising a unitary piece of soft, flexible polymeric foam, said element having a longitudinal medial axis, a peripheral wall, first and second sides, and first and second ends, said element further comprising:

(a) a first peripheral wall portion of said first side a first predetermined distance away from said longitudinal medial axis;

(b) a first retaining means for retaining said needle, said first retaining means comprising a second peripheral wall portion at or near said first end on said first side, a second predetermined distance from said longitudinal medial axis that is less than said first predetermined distance away from said longitudinal medial axis;

(c) a second retaining means remote from said first retaining means for retaining said first portion of said strand, said second retaining means being at or near said first end; and (d) securing means remote from said first and second retaining means for frictionally engaging said second portion of said suture strand when said strand is extended relatively tautly from said first retaining means to said securing means to said second retaining means, said securing means being within the body of said element.

7 Claims, 6 Drawing Figures

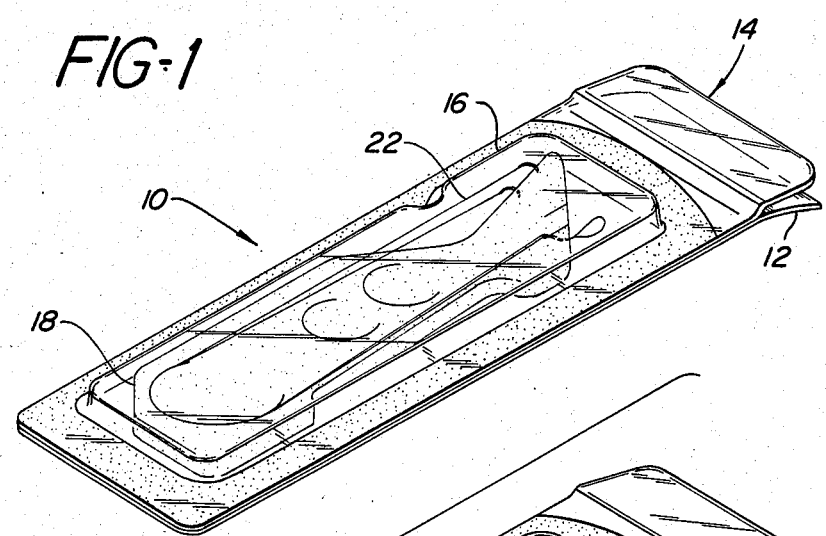
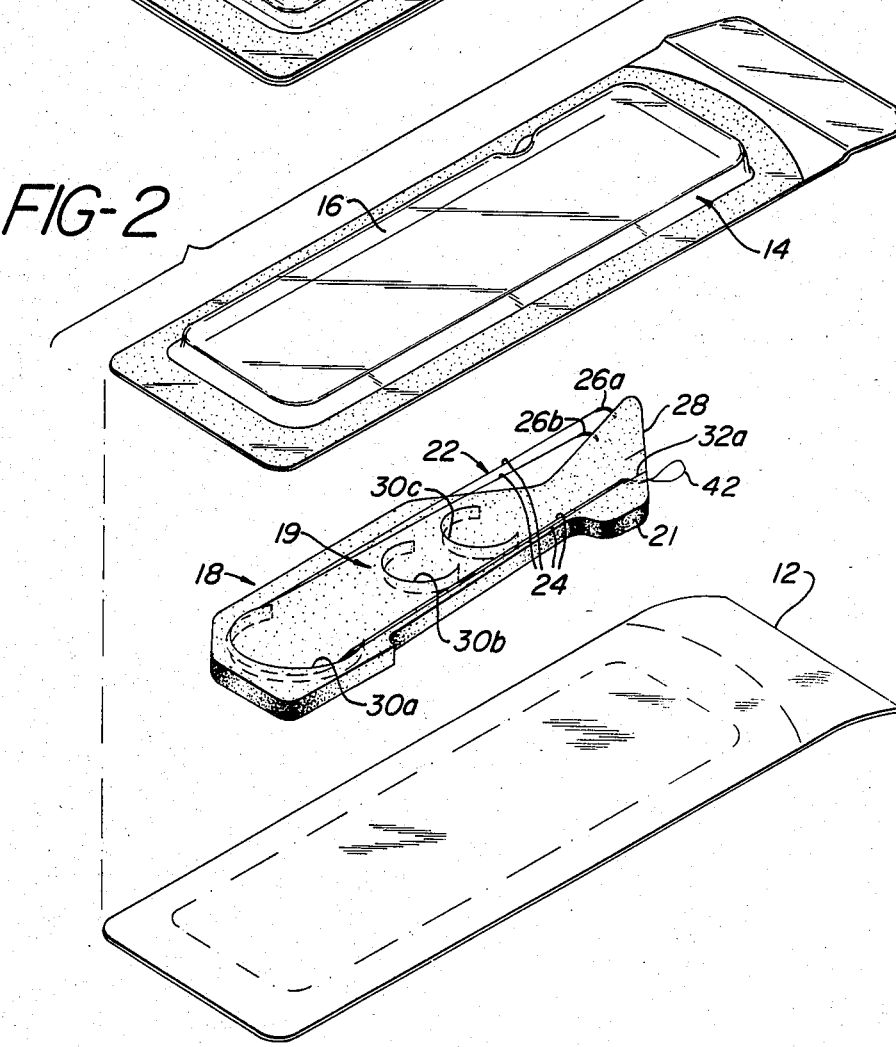

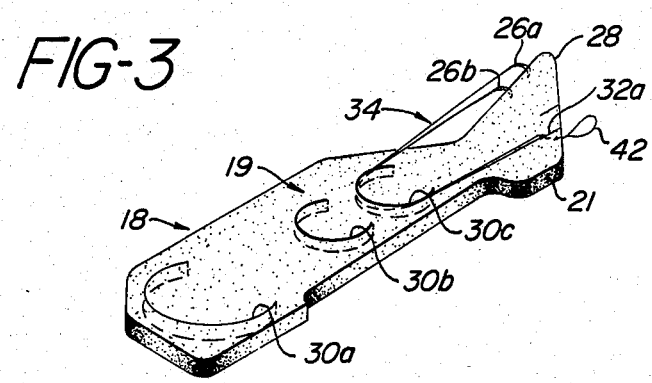
FIG-3
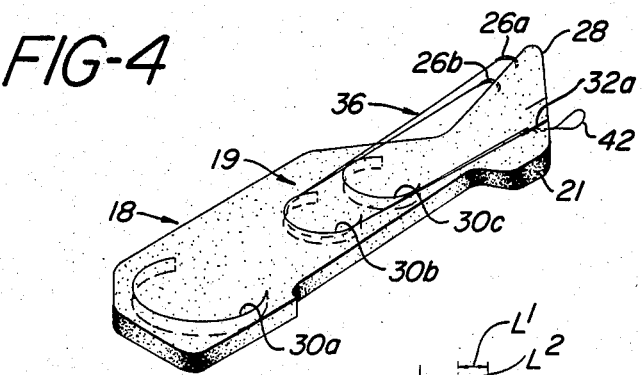
FIG-4
FIG-5
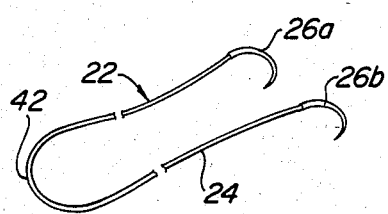
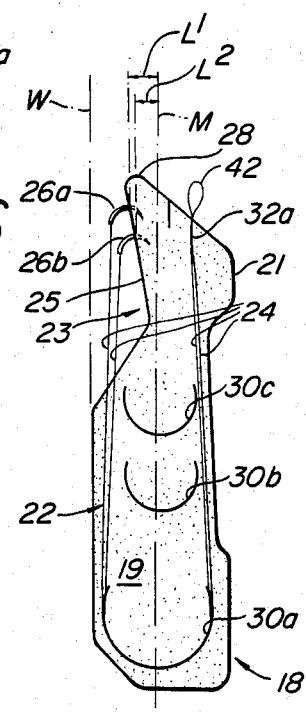
FIG-6

UNITARY ARMED SUTURE MOUNTING BOARD

This application is a continuation-in-part of copending application Ser. No. 555,724, filed Nov. 28, 1983.

The invention relates to a board for mounting armed sutures, and more particularly, to a package utilizing the same.

BACKGROUND OF THE INVENTION

Packages for surgical sutures are designed and constructed according to the nature of the suture and its intended use. The ideal package holds and protects the suture during handling and storage, and still allows the suture to be readily removed with a minimum of handling that could impair the suture.

Very fine sutures, such as those that are intended for use in ophthalmic surgery, have special requirements owing to the very fine size of the needles and small diameter of the suture strands, often as small or smaller than a human hair. For instance, while it is desired to hold the suture firmly in place in the package to prevent entangling of the strand, it is also necessary to be able to remove the suture without damage to the needle or without fraying or weakening the strand.

The present invention is directed to a suture mounting board and to a package utilizing the same that is particularly adapted for use with very fine size sutures.

BRIEF SUMMARY OF THE INVENTION

The invention provides an element for holding a needled suture comprising a suture strand having at least one end attached to a needle and having a first portion of said suture strand remote from the end attached to said needle and a second portion of said suture strand intermediate said first portion and the end attached to said needle, said element comprising a unitary piece of soft, flexible polymeric foam, said element having a longitudinal medial axis, a peripheral wall, first and second sides, and first and second ends, said element further comprising:
  (a) a first peripheral wall portion of said first side a first predetermined distance away from said longitudinal medial axis;
  (b) a first retaining means for retaining said needle, said first retaining means comprising a second peripheral wall portion at or near said first end on said first side, a second predetermined distance from said longitudinal medial axis that is less than said first predetermined distance away from said longitudinal medial axis;
  (c) a second retaining means remote from said first retaining means for retaining said first portion of said strand, said second retaining means being at or near said first end; and
  (d) securing means remote from said first and second retaining means for frictionally engaging said second portion of said suture strand when said strand is extended relatively tautly from said first retaining means to said securing means to said second retaining means, said securing means being within the body of said element.

The invention also provides a suture package which utilizes the above-described element.

THE PRIOR ART

In Mandel et al., U.S. Pat. No. 4,120,395, there is disclosed a package for double-armed sutures, particularly ophthalmic sutures, comprising a one-piece folded packet having needle mounting means and suture loop retaining means which are readily accessible when the package is opened. Both the needle mounting means and the loop retaining means can be pieces of soft polymeric foam having slits therein.

Thyen, in U.S. Pat. No. 4,135,623, shows a package for double-armed sutures.

Schmidt et al., U.S. Pat. No. 4,183,431, disclose a foam mounting element for needled sutures in which the needle is inserted into an edge and the threads are inserted in slits at the bottom of the element.

BRIEF DESCRIPTION OF THE DRAWINGS

FIG. 1 is a perspective drawing of a suture package illustrating a preferred embodiment of the invention;

FIG. 2 is an exploded view of the package of FIG. 1;

FIG. 3 is a perspective view of the suture mounting element shown in FIG. 1, shown with a different length suture, FIG. 4 is a view similar to FIG. 3 wherein a still different length suture is shown mounted thereon;

FIG. 5 shows a double armed suture folded in half, ready to be mounted on a mounting board in accordance with the principles of the invention; and FIG. 6 is a top plan view of the suture mounting element shown in FIG. 1.

DETAILED DESCRIPTION OF THE INVENTION

As used herein, the term "suture" means elongated, thread-like strands suitable for suturing, ligating, or other surgical procedures, with or without needles attached. A "single-armed suture" is a suture having a needle affixed to one end, and the term "double-armed suture" refers to a suture having needles attached to both ends. The term "suture strand" refers specifically to the elongated thread-like portion of the suture.

Referring now to the drawings, FIGS. 1 and 2 show a suture package 10 containing a suture mounting element 18 that embodies the principles of the invention. The package 10 contains a rear panel 12 bonded to a front panel 14, which is preferably made of clear plastic. The rear panel 12 may be made of a material such as spunbonded polyolefin that is a bacterial barrier but is pervious to sterilizing gas, to facilitate sterilization of the package. The front panel 14 has a blister 16 molded in it which, together with the rear panel 12, defines a suitable storage compartment. Within the suture storage compartment there is a mounting element 18 made from a single piece 19 of soft, flexible, polymeric foam, such as polyethylene foam, which, in an alternative embodiment (shown in FIGS. 5 and 6), may be bonded to a paperboard backing 20, which acts as a stiffening element. Mounted on the mounting element 18 is a double-armed suture 22 comprising a strand 24 and two needles 26a, 26b.

The suture 22 is mounted on the mounting element 18 in the following manner:

The points of the two needles 26a, 26b are inserted in the foam 19 near one end 28 of the foam 19, as is shown in the Figures. The doubled suture strand 24 is held relatively tautly so that the strand 24 is held under slight tension from the mounted needles 26a, 26b, and the tautly held strand 24 is pressed into a round slit 30a that is cut in the foam 19. The strand 24 is then held under slight tension from the slit 30a, and the end 42 of the doubled strand 24 is inserted in a slit 32a at the same end 28 of the foam 19 at which the needles 26a, 26b are inserted, but on the opposite side. By mounting the suture 22 in this manner, it is held firmly in a protected manner so that it is easy for the surgeon to remove the suture 22 from the element 18. The invention is particularly useful from packaging and storing very fine sutures such as those that are used in ophthalmic surgery because such fine sutures are held firmly in place, and do not tend to "float", until the surgeon is ready to use them.

Referring now to FIG. 6, the advantages of the invention, and the features of the invention that contribute most significantly to these advantages, can be most readily seen.

In FIGS. 3 and 4 there are shown sutures 34, 36 having different lengths than the suture 22 shown in FIGS. 1 and 6. The needles 26a and 26b are embedded in the foam 19 in the peripheral wall 21 thereof (see FIG. 2) in a cut out portion, shown generally in FIG. 8 as 23. The needle 26a that is mounted closest to the end 28 is located closer to the longitudinal medial axis M than an imaginary line W that is parallel to the longitudinal medial axis M and extends from the peripheral wall 21 of the foam 19 on the same side as the cut out portion 23 and at the point where said peripheral wall 21 is the greatest distance from the longitudinal medial axis M. The needle 26a is thus better protected than it would be if it extended beyond the said imaginary line W. The peripheral wall portion 25, into which the first needle 26a is inserted, extends diagonally with respect to the longitudinal medial axis M such that the second needle 26b, which is inserted in the wall portion 25 slightly farther away from the needle end 28 of the foam 19, is slightly closer to the longitudinal medial axis M than is the first needle 26a. Thus, the distance $L^2$ is slightly less than the distance $L^1$. (The distance $L^1$ and $L^2$ are the distances from the points of insertion into the wall portion 19 to the longitudinal medial axis M of the first and second needles 26a and 26b, respectively.) For this reason, the portion of the suture strand 24, extending from the two needles 26a and 26b to the slit 30a into which the strand 24 is inserted, are separated and not superimposed, thus making it easier for the surgeon to grasp only one needle or one portion of the strand.

Except for the end 42 of the doubled strand 24, the entire suture 22 is contained within the overall outline of the mounting element 18, and is thereby protected. This is important for very fine sutures to prevent damage and/or entangling.

The invention is useful for packaging both single-armed and double-armed sutures, although its use with very fine, double-armed sutures is preferred.

The invention has the virtue of simplicity of design and operation. It also has the advantage of visually presenting the suture to the surgeon before the package is opened, so the surgeon can make sure that the correct size and length suture is contained therein before the sterile package is opened.

What is claimed is:

1. An element for holding a needled suture, said suture comprising a suture strand having at least one end attached to a needle and having a first portion of said strand remote from the end attached to said needle and a second portion of said strand intermediate said first portion and the end attached to said needle, said element comprising a unitary piece of soft flexible polymeric foam, said element having a longitudinal medial axis, a peripheral wall, first and second sides and first and second ends, said element further comprising:
    (a) a first peripheral wall portion of said first side a first predetermined distance away from said longitudinal medial axis;
    (b) a second peripheral wall portion of said first side at or near said first end, said second peripheral wall portion being a second predetermined distance from said longitudinal medial axis that is less than said first predetermined distance away from said longitudinal medial axis, said second peripheral portion thereby comprising a cut out portion of said first side;
    (c) a first retaining means for retaining said needle, said first retaining means being in said second peripheral wall portion;
    (d) a second retaining means spaced from said first retaining means for retaining said first portion of said strand, said second retaining means being at or near said first end; and
    (e) securing means remote from said first and second retaining means for frictionally engaging said second portion of said suture strand when said strand is extended relatively tautly from said first retaining means to said securing means to said second retaining means, said securing means being within the body of said element.

2. The element of claim 1 wherein said first retaining means comprises said soft, flexible polymeric foam, whereby the point of said needle is inserted in said foam.

3. The element of claim 1 wherein said second retaining means comprises a slit in said foam.

4. The element of claim 1, 2, or 3 wherein said securing means comprises a slit in said foam.

5. The element of claim 1, 2, or 3 wherein the suture is a double-armed suture having first and second needles, wherein the first needle is retained in said first retaining means said second predetermined distance away from said longitudinal axis, and wherein the second needle is retained in said first retaining means a third predetermined distance away from said longitudinal axis that is les than said second predetermined distance away from said longitudinal axis.

6. A suture package comprising a rear panel bonded to a front panel, containing a needled suture mounted on the element of claim 1.

7. The suture package of claim 6 in sterile condition.

* * * * *